(12) United States Patent
Clark et al.

(10) Patent No.: US 11,686,716 B2
(45) Date of Patent: Jun. 27, 2023

(54) FLOW CELL

(71) Applicant: LINCOLN AGRITECH LIMITED, Lincoln (NZ)

(72) Inventors: Claire Mary Clark, Rolleston (NZ); Neil Francis Pasco

(73) Assignee: Lincoln Agritech Limited, Lincoln (NZ)

( * ) Notice: Subject to any disclaimer, the term of this patent is extended or adjusted under 35 U.S.C. 154(b) by 295 days.

(21) Appl. No.: 16/648,196

(22) PCT Filed: Sep. 19, 2018

(86) PCT No.: PCT/NZ2018/050125
§ 371 (c)(1),
(2) Date: Mar. 17, 2020

(87) PCT Pub. No.: WO2019/059782
PCT Pub. Date: Mar. 28, 2019

(65) Prior Publication Data
US 2020/0284777 A1    Sep. 10, 2020

(30) Foreign Application Priority Data
Sep. 19, 2017  (NZ) ......................... 735630

(51) Int. Cl.
*G01N 33/04* (2006.01)
*G01N 27/327* (2006.01)

(52) U.S. Cl.
CPC .......... *G01N 33/04* (2013.01); *G01N 27/327* (2013.01); *G01N 27/3271* (2013.01); *Y10T 436/117497* (2015.01); *Y10T 436/2575* (2015.01)

(58) Field of Classification Search
CPC .............. G01N 27/308; G01N 27/327; G01N 27/3271; G01N 33/04; G01N 33/54366;
(Continued)

(56) References Cited

U.S. PATENT DOCUMENTS 2,810,835 A * 10/1957 Miller ................ G01N 21/314
                                                    250/345
9,150,907 B2   10/2015 Shaikh et al.
(Continued)

FOREIGN PATENT DOCUMENTS

PL            231318 B1    2/2019
WO       2011/132164 A1   10/2011
(Continued)

OTHER PUBLICATIONS

Santos et al. Electrophoresis, vol. 35, pp. 864-869, 2014.*
(Continued)

*Primary Examiner* — Maureen Wallenhorst
(74) *Attorney, Agent, or Firm* — TraskBritt (57) ABSTRACT

A flow cell with a first section and a second section, and a gasket sealing between the first and second sections. A chamber is defined in the flow cell, having a perimeter with a narrower end and a rounded wider end. An inlet passage, outlet passage, and a sensor are arranged in fluid communication with the chamber. The inlet passage directs fluid into the chamber proximal its narrow end at an angle of between about 45° and 75° relative to the plane of gasket and the outlet passage directs fluid flow out of the wider end of the chamber at an angle between about 45° and 75° relative to the plane of gasket, the inlet passage and outlet passage being angled in opposite directions. The flow cell is useful for monitoring levels of chemicals in an industrial process stream, such as lactose levels in a dairy process stream.

29 Claims, 10 Drawing Sheets

(58) Field of Classification Search
CPC .. Y10T 436/115831; Y10T 436/117497; Y10T 436/12; Y10T 436/2575
USPC .. 436/20, 22, 23, 50, 52, 55, 149, 150, 180; 422/63, 67, 74, 81, 82.01, 82.02, 502, 422/503, 509
See application file for complete search history.

(56) References Cited

U.S. PATENT DOCUMENTS

| | | | |
|---|---|---|---|
| 2004/0018116 A1* | 1/2004 | Desmond | C12Q 1/686 422/502 |
| 2009/0224482 A1 | 9/2009 | Nurse | |
| 2014/0373606 A1* | 12/2014 | Kraiczek | G01N 33/54373 156/60 |
| 2017/0173588 A1* | 6/2017 | Tang | B01L 3/50273 |
| 2019/0056312 A1* | 2/2019 | Arnone | G01N 21/05 |
| 2019/0160466 A1 | 5/2019 | Yamagata et al. | |

FOREIGN PATENT DOCUMENTS

| | | | |
|---|---|---|---|
| WO | 2015/175189 A1 | | 11/2015 |
| WO | 2016/153428 A1 | | 9/2016 |
| WO | 2017/060088 | * | 4/2017 |

OTHER PUBLICATIONS

Glithero et al. Analytical Bioanalytical Chemistry, vol. 405, pp. 3791-3799, 2013.*

Anonymous: "QCMT Flow cell kit—Measurement Example", Oct. 21, 2016 (Oct. 21, 2016), pp. 1-2, XP055790438, Retrieved from the Internet: URL:https://web.archive.org/web/20161021001646/https://www.als-japan.com/1403.html.

Anonymous: "QCMT Flow Cell Kit", [retrieved from the internet on Dec. 21, 2018] https://web.archive.org/web/20161021001646/https://www.als-japan.com/1403.html, published Oct. 26, 2016 as per Wayback Machine Application Tab, Schematic of EQCM Measurement System Figure, QCM Flow Mode Figure, Top of Page Figure, 2 pages.

Anonymous: "QMCT Flow cell kit", Oct. 21, 2016 (Oct. 21, 2016), pp. 1-2, XP055790409, Retrieved from the Internet: URL:https://web.archive.org/web/20161021001646if_/https://www.als-japan.com/1403.htm.

Carroll et al., "Microfabricated electrochemical sensors for exhaustive coulometry applications." Sensors and Actuators B: Chemical 160, No. 1 (2011): 318-326.

DropSens, L.C., Accessories: Cells, "Flow-Cell for Screen-Printed Electrodes", ref. FLWCL, http://www.dropsens.com/pdfs_productos/flowcell.pdf, [retrieved from internet on Mar. 17, 2020], 2 pages.

European Search Report and Search Opinion Received for EP Application No. 18858736, dated Apr. 7, 2021, 10 pages.

Instruction Manual For Bas Epsilon Lc Systems, Installation, Flowcells, [retrieved from the internet Mar. 17, 2020] https://www.basinc.com/manuals/LC_epsilon/Installation/Flowcell/flowcell, 2006 Bioanalytical Systems, 7 pages.

International Search Report for International Application No. PCT/NZ2018/050125, dated Dec. 24, 2018, 4 pages.

International Written Opinion for International Application No. PCT/NZ2018/050125, dated Dec. 24, 2018, 5 pages.

Jarosova et al, "Evaluation of a nitrogen-incorporated tetrahedral amorphous carbon thin film for the detection of tryptophan and tyrosine using flow injection analysis with amperometric detection", Analyst, vol. 141, No. 21, Jan. 1, 2016 (Jan. 1, 2016), pp. 6031-6041, XP055584499.

Pike et al, "Flow Cell Design for 6 Effective Biosensing", Sensors, vol. 13, No. 1, Dec. 20, 2012 (Dec. 20, 2012), pp. 58-70, XP055500041.

* cited by examiner

FLOW CELL

CROSS-REFERENCE TO RELATED APPLICATIONS

This application is a national phase entry under 35 U.S.C. § 371 of International Patent Application PCT/NZ2018/050125, filed Sep. 19, 2018, designating the United States of America and published as International Patent Publication WO 2019/059782 A1 on Mar. 28, 2019, which claims the benefit under Article 8 of the Patent Cooperation Treaty to New Zealand Patent Application Serial No. 735630, filed Sep. 19, 2017.

TECHNICAL FIELD

The present disclosure relates to a flow cell for receiving a fluid stream and determining the concentration of one or more chemicals in the fluid. In particular, the present disclosure relates to a flow cell incorporating at least one biosensor for the accurate measurement of the concentration of a chemical, such as lactose, in an industrial process stream, such as a dairy process stream.

BACKGROUND

The dairy industry relies heavily on a variety of large-scale processing technologies for the processing of milk into numerous different dairy products. All processes employed have the potential to suffer from inefficiencies, which may be caused by a variety of factors including system failures, leaks, spills, equipment cleaning, and the frequency of start-up and shut-down cycles and clean-in-place cycles. A consequence of these inefficiencies is often the loss of processing volume. The dairy industry currently accepts that 2.5% of total processing volume is lost during processing. A reduction in this loss of even 10% may equate to savings in the order of billions of dollars for the dairy industry globally. Furthermore, many of the factors noted above result in processing volume having to be diverted to waste. A reduction in waste consequently reduces the environmental impact of dairy processing. There is therefore a continuing demand for improvements in dairy processes. One important aspect of the optimization of dairy processes is the monitoring of levels of certain components of the process stream, e.g., lactose, typically measured using an analytical test (e.g., HPLC) in the laboratory rather than via in-process monitoring. However, in order that dairy processes can be optimized effectively, the concentration of a chemical component needs to be monitored accurately and with rapid or real-time feedback to a control system so that process parameters can be adjusted.

Ideally, the monitoring is in-process monitoring to avoid the wastage of time and effort associated with extracting samples from process streams, measuring the concentration of a component in the samples, and then feeding information to a control system. Flow cells are typically used for in-process monitoring. They will have an inlet for receiving a portion of the process stream and an outlet from which the portion is returned to the process stream. They will have a means for sensing or detecting the amount of a specified component in the stream. They will usually comprise electrical circuitry connected to a sensor for the purpose of recording an output from the sensor and transmitting signal data to a control system. Such flow cells will require a gasket to provide a seal between components of the flow cell as well as a means for controlling the in-flow and out-flow of sample stream and contact between the sample stream and the sensor.

One problem associated with many flow cells is interference due to the presence of air bubbles, which adversely affect the accuracy of concentration measurements. It is therefore important that the flow through the flow cell is laminar rather than turbulent. Leakage is another problem with many flow cells. Any leakage of sample stream is likely to lead to corrosion at certain sites of the flow cell and to a limited lifetime for sensors used in the flow cell. Different types of flow cells have different strengths and weaknesses. Often the choice of flow cell comes down to the application and the type of sensor used.

Some flow cells have inlet and outlet flow paths that are orientated at 90° to the plane of the gasket. One example is the Epsilon flow cell available from Bioanalytical Systems, Inc. (https://www.basinc.com/manuals/LC_epsilon/Installation/Flowcell/flowcell). However, flow paths at 90° to the plane of the gasket are considered to contribute to the problem of turbulent flow and therefore the problem of air bubbles present in the stream. Pike, et al., Sensors, 2013, 13, 58-70, describes a flow cell having 90° flow paths and discusses reduced flow cell efficiency with increasing flow rates. This is related to the increased importance of diffusion (the process by which matter moves down a concentration gradient, from an area of high concentration to an area of low concentration) relative to advection (transfer of matter by flow), with efficiency being limited by the development of regions of recirculating flow (eddies).

Some flow cells have inlet and outlet flow paths that are not perpendicular to the gasket or sensor. For example, a flow cell available from DropSens, L.C. (http://www-.dropsens.com/pdfs_productos/flowcell.pdf) has an inlet flow perpendicular to the surface of an electrode, but an outlet flow path at an angle of approximately 45°. But this flow cell (a wall jet flow cell) operates on the basis of a jet of fluid that strikes a planar surface at right angles and spreads out radically over that surface. The fluid in the jet is highly turbulent while the fluid outside the jet is purportedly laminar. The outlet of a wall jet flow cell must be at an angle other than 90° as there is no other space for the liquid to be removed. The turbulent nature of fluid entering the flow cell creates bubbles, which impedes accurate measurement by the sensor.

A flow cell described in Santos, et al., Electrophoresis, 2014, 35(6), has inlet and outlet paths at 45° to the plane of the gasket. Another example is the flow cell described in Jarosova et al., Analyst, 2016, 141, 6031-6041. While not explicitly disclosed in these publications, it is assumed that at least the inlet is angled to provide a more gentle flow onto and over the sensor, or perhaps that that the inlet and outlet are angled to avoid dead volumes.

Gasket design has been found to be important for optimal operation of a flow cell. Gaskets classically incorporate a rectangular or circular opening that define the contact area between fluid and sensor. However, alternative designs have been developed in recent years. U.S. Ser. No. 12/397,697, now abandoned, describes a gasket for use in a flow cell, which defines a space having angled or wedge-shaped ends so as to provide a zero dead volume flow path in a flow cell. U.S. Pat. No. 9,150,907 describes microfluidic flow cell assemblies for encapsulating a sample where the shape of the gasket employed may be generally rectangular but with rounded ends. Carroll, S., et al. Sensors and Actuators B 160(2011), 318-326, reports an evaluation of different flow cell configurations including one incorporating a gasket with an elliptical hole. The elliptical shape of the hole is the to promote laminar flow within the flow cell and complete clearing of the cell by eliminating corner areas where air bubbles and stagnant pools of sample might collect.

The efficiency of three different biosensor flow cells is reported in Pike et al., Sensors, 2013, 13, 58-70. All three flow cells feature a central channel that expands in the vicinity of the sensing element to provide the same diameter active region, but the rate of channel expansion and contraction varies between the designs. Three different gasket designs (square, circular and eye-shaped) were examined in terms of eddy development at different flow rates with a flow cell that has 90° inlet and outlet flow paths. It was concluded that the behavior of a flow cell, measured in terms of its response to the incoming fluid, is critically dependent on both the shape of the flow cell and the flow rate of the influent, and that a flow cell with a smooth profile between the inlet and outlet outperformed those flow cells based on circular or square profiles.

However, although alternative gasket shapes have been investigated, non-laminar fluid flow continues to be a problem and there is room for further optimization of gasket design. For example, a key factor in optimal biosensor flow cell design is the kinetics of the biosensor. Biosensor kinetics depends primarily on the rates of ligand-receptor association and dissociation, which must be considered relative to the flow cell response rate. A sensor with fast kinetics relative to the flow cell response rate will respond "instantaneously" to the cell concentration, but time for equilibration must be allowed when the kinetics are slow. Third generation biosensors work via direct electron transfer. Other enzyme biosensors are first generation or second generation biosensor. First generation biosensors transfer electrons to molecular oxygen and the resulting decrease in the oxygen concentration and/or the concentration of hydrogen peroxide produced is measured. In second generation biosensors, artificial partially toxic mediators or nanomaterials are used to transport electrons to an electrode. Diffusion is less important for third generation biosensors than first and second generation biosensors as electrons are not transferred to the electrode via a substance in solution.

Thus, there are a multitude of variables that must be considered for optimal flow cell design. The applicant has now developed a flow cell comprising an arrangement of a gasket and fluid inlet and outlet paths that goes some way to addressing the problems associated with known flow cells. It is therefore an object of the present disclosure to provide such a flow cell, or to at least provide a useful alternative to existing flow cells.

BRIEF SUMMARY

A first aspect of the present disclosure provides a flow cell comprising a first body section and a second body section, and a gasket arranged to seal between the first section and the second section. The gasket, the first section, and the second section together define one or more chambers, each chamber having a perimeter with a narrower end and a rounded wider end. Each chamber has an associated inlet passage in fluid communication with the chamber, an associated outlet passage in fluid communication with the chamber, and a sensor arranged in fluid communication with the chamber.

Each inlet passage directs fluid into the respective chamber proximal the narrow end of the chamber at an angle of between about 45° to about 75° relative to the plane of gasket, and each outlet passage directs fluid flow out of the wider end of the chamber at an angle between about 45° to about 75° relative to the plane of gasket, with the inlet passage and outlet passage being angled in opposite directions to each other. The flow cell further comprises an electronic measurement system in electrical communication with each of the one or more sensors and configured to transmit data to a data processor.

In an embodiment, the electronic measurement system comprises a potentiostat printed circuit board.

The gasket may comprise one or more apertures shaped to define the perimeter of a respective chamber. In an embodiment, the depth of each chamber substantially corresponds to the thickness of the gasket.

In an embodiment, the inlet and outlet passages are provided in the first body section. Alternatively the inlet and outlet passages may be provided in the second section, or one of the inlet or outlet passages may be provided in the first section and the other of the inlet or outlet passages may be provided in the second section.

In an embodiment, the second body section comprises one or more recesses to receive the sensor(s). Alternatively the one or more recesses for the sensor(s) may be provided in the first section. The sensor may project partly from the recess or may sit substantially flush with the surface surrounding the recess. The sensor may be provided on a sensor support such as a tile, the sensor support being received by the recess. Preferably the dimensions of the recess complement the dimensions of the sensor support.

In an embodiment, each chamber is tear-shaped.

In an embodiment the gasket comprises a deformable and/or resilient material. In one exemplary embodiment, the gasket comprises silicone. In alternative embodiments, the gasket may comprise one or more of rubber, silicone, nitrile rubber, neoprene, polytetrafluoroethylene (PTFE), or other suitable material, Polydimethylsiloxane (PDMS) and plastics polymers such as polychlorotrifluoroethylene.

In an embodiment, each inlet passage, respective chamber, and respective outlet passage defines a fluid flow path, the fluid flow path along the inlet passage and the chamber forming an angle of at least about 105°, and the fluid flow path along the chamber and outlet passage forming an angle of at least about 105°. In an embodiment, the fluid flow path along the inlet passage and the chamber forms an angle of between about 105° and about 135°, preferably between about 115° and about 125°, for example, about 120°. In an embodiment, the fluid flow path along the chamber and outlet passage forms an angle of between about 105° and about 135°, preferably between about 115° and about 125°, for example, about 120°.

In an embodiment, each inlet passage is configured to be below the associated outlet passage, for example, such that the inlet passage, respective chamber, and respective outlet passage defines a fluid flow path in a generally upwards direction.

In an embodiment, the inlet and outlet passages and chambers enable substantially laminar flow of liquid along each chamber. In an embodiment, the laminar flow occurs when the fluid flow rate through each chamber is within a working range of the flow cell, for example, less than 40 µL $s^{-1}$, or between about 10 µL $s^{-1}$ and about 30 µL $s^{-1}$.

In an embodiment, the angle of fluid flow from each fluid inlet passage to each respective chamber and/or from each chamber to each respective fluid outlet passage, relative to the plane of gasket, is in the range of about 55° to about 65°, preferably about 60°.

In one embodiment, the flow cell comprises two to eight sensors, for example, four sensors. However, different embodiments may comprise only a single sensor or more than eight sensors depending on the intended application.

In an embodiment, the sensor is a biosensor. Each biosensor may comprise a sensor molecule immobilized on a screen-printed electrode. The sensor molecule may be selected from the group comprising microorganisms, organelles, cell receptors, enzymes, antibodies, and nucleic acids. In an embodiment, the biosensor is capable of determining the concentration of a chemical in a fluid independently of each other biosensor in the array.

In an embodiment, at least one of the biosensors is capable of determining the concentration of any one or more of the group comprising pesticides, fertilizers, oxylate, amygdalin, glucoalcalides, glucose, fructose, lactose, sucrose, lactate, lactulose, glutamate, lysine, malate, ethanol, glycerol, catechol, cholesterol, citric acid, lecithin, polyphenols, short chain fatty acids, ornithine, amines, hypoxanthine, lactic acid, and isocitrate. In an embodiment, at least one of the biosensors is capable of determining the concentration of lactose.

The flow cell may further include a cover for protection of the electronic measurement system.

In an embodiment, the fluid is a liquid.

A second aspect of the present disclosure provides a method for determining the concentration of a chemical in a fluid obtained from a process stream comprising placing a flow cell as described above in relation to the first aspect, in fluid communication within a flow of fluid from the process stream, and transmitting measurement data from the electronic measuring system to a processor.

The chemical may be selected from the group comprising pesticides, fertilizers, oxylate, amygdalin, glucoalcalides, glucose, fructose, lactose, sucrose, lactate, lactulose, glutamate, lysine, malate, ethanol, glycerol, catechol, cholesterol, citric acid, lecithin, polyphenols, short chain fatty acids, ornithine, amines, hypoxanthine, lactic acid, and isocitrate.

In one embodiment of the method, the fluid is a liquid obtained from a dairy processing stream.

In one embodiment, a biosensor located in the flow cell may be used to determine the concentration of the chemical, which biosensor has electrodes that are in electrical communication with a potentiostat printed circuit board.

In one embodiment, a data processor processes the data received from the biosensor and produces an output to enable a controller to adjust one or more parameters of a process that produces the process stream.

A second aspect of the present disclosure provides a system comprising the flow cell described above, arranged in communication with fluid from a process stream, a processor in communication with the flow cell electronic measurement system, and a controller configured to receive an output from the processor and adjust the one or more parameters of a process that produces the process stream in response to the processor output, wherein the processor output is representative of a concentration of a chemical in the fluid obtained from the process stream.

BRIEF DESCRIPTION OF THE DRAWINGS

Embodiments will now be described by way of example only and with reference to the accompanying drawings in which.

DETAILED DESCRIPTION

The present disclosure relates to a flow cell, embodiments of which may be able to provide real time, location-specific, interference-free in-process monitoring of process streams such as wastewater and other streams from industrial processes. Referring to FIGS. 1 to 4C, the flow cell 1 comprises a first body section 2 and a second body section 3, and a gasket 5 arranged to sit between the first section 2 and the second section 3, forming a seal. The gasket 5, the first section 2, and the second section 3 together define one or more chambers, each chamber having a perimeter with a narrower end and a rounded wider end. Each chamber has an inlet passage 9 in fluid communication with the chamber, an outlet passage 10 in fluid communication with the chamber, and a sensor 11 arranged in fluid communication with the chamber. Each inlet passage 9 directs fluid into the respective chamber proximal the narrow end of the chamber at an angle of between about 45° to about 75° relative to the plane of gasket and each outlet passage 10 directs fluid flow out of the wider end of the chamber at an angle between about 45° to about 75° relative to the plane of gasket, the inlet passage and outlet passage being angled in opposite directions. The flow cell 1 further comprises an electronic measurement system in electrical communication with each of the one or more sensors and configured to transmit data to a data processor.

Figure 4A:
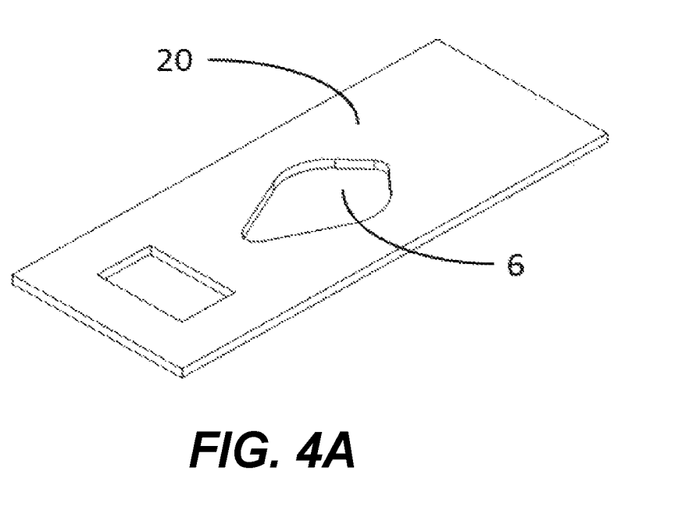
FIG. 4A is a perspective view showing one embodiment gasket for a flow cell, having a single opening for defining a chamber.

The term "teardrop shape" is intended to mean any shape that has a generally round wide end and a generally narrow tapered end. One example of a teardrop shape is shown in FIG. 4C where the shape is defined by three circles and the relationship between them. It will be appreciated that the teardrop shape as used in connection with the present disclosure is not limited to the shape of FIG. 4C or any specifically defined shape, but includes any shape having a round end and a narrow end and has the function of encouraging laminar fluid flow when introduced into and moving through a chamber having a teardrop shape.

The term "diffusion" is intended to mean the movement of a substance from a region of higher concentration to a region of lower concentration.

The term "advection" is intended to mean the transfer of heat or matter by the flow of a fluid.

The term "printed circuit board" or "PCB" is intended to mean a support comprising electronic components electrically connected using conductive tracks, pads and other features etched typically from copper sheets laminated onto a non-conductive substrate. A potentiostat PCB is a PCB incorporating electronic componentry to control a three-electrode cell.

The term "biosensor" is intended to mean an analytical device, which uses a living organism or biological molecule, especially an enzyme or antibody, to detect the presence of chemicals and convert the response into an electrical signal.

A key aspect of the flow cell of the present disclosure is the combination of the teardrop shape of openings in the gasket and the angled orientation of the fluid inlets and fluid outlets. This combination encourages laminar flow of the fluid and minimizes the formation of eddies or bubbles in the chambers where accurate measurement by the sensors is important. Bubbles and turbulent flow in these regions leads to inaccuracies in sensor measurement and consequently optimal monitoring and control of industrial processes is not possible. The use of teardrop-shaped openings in the gasket to produce a gradually expanding chamber above the sensor results in analyte diffusion instead of advection helping to create a laminar flow at the working electrode surface of the sensor.

The angle of fluid flow into and out of each chamber, relative to the plane of gasket, is in the range 45-75°. It will be appreciated that this angle may be varied depending on the particular flow cell design and application. For example, the angle may be in any range within 45-75° including, but not limited to, 45-70°, 45-65°, 45-60°, 45-55°, 45-50°, 50-75°, 50-70°, 50-65°, 50-60°, 50-55°, 55-75°, 55-70°, 55-65°, 55-60°, 60-75°, 60-70°, 60-65°, 65-75°, and 65-70°. Preferably, the angle is in the range 55-65°, and, for example, may be 55°, 56°, 57°, 57°, 58°, 59°, 60°, 61°, 62°, 63°, 64°, or 65°.

Further, it will be appreciated that the angle of fluid flow into each chamber may be the same as or different from the angle of fluid flow out of each chamber.

The flow cell comprises a housing for an array of one or more sensors. While a flow cell having a single sensor may be adequate for a particular application, it is preferred that the flow cell will house an array of 2, 3, 4, 5, 6, 7, 8 or more sensors. One benefit of multiple sensors in a flow cell is that the life of the flow cell is effectively extended relative to a flow cell having fewer sensors. An extended life of a flow cell means reduced maintenance due to less frequent replacement of the flow cell in an industrial setting or less frequent replacement of sensors in the flow cell. The operation of the flow cell can be controlled so that one sensor is used until it reaches the end of its effective life and then a different sensor in the array is used. For example, in the case of a flow cell having four sensors, the fluid stream may be directed via computer control to a first chamber containing a first sensor and then, after a period of time, to a second chamber containing a second sensor and then, after a further period of time, to a third chamber, and so on.

The biosensors used in the flow cell of the present disclosure will be any biosensors suitable for sensing and measuring the concentration of certain chemicals in the fluid stream. In some embodiments of the present disclosure the sensor molecule of the biosensor is in solution. In other embodiments the sensor molecule is immobilized on a screen printed carbon electrode (SPCE). The sensor molecule may be selected from the group comprising microorganisms, organelles, cell receptors, enzymes, antibodies, and nucleic acids.

The biosensor is typically an SPCE incorporating an immobilized enzyme. The enzyme may be selected from the group comprising oxidoreductases, transferases, hydrolases, lyases, isomerases, and ligases. In some embodiments of the present disclosure the enzyme displays direct electron transfer (DET) behavior (i.e., a third generation biosensor) and is selected from the oxidoreductases group of enzymes comprising dehydrogenases, hydrogenases, reductases, oxidases, peroxidases and laccases. For example, an SPCE incorporating immobilized cellobiose dehydrogenase may be used for determining lactose concentration in the fluid.

The flow cell of the present disclosure is intended to be used in a vertical orientation so that the chambers are orientated vertically and each fluid inlet is located at or near the bottom end of the chamber and each fluid outlet is located near at or near the top end of the chamber. Thus, the fluid stream will enter the chamber at or near the bottom of the chamber and will exit the chamber at or near the top of the chamber. This means that the flow of the fluid stream is in the same direction as the movement of any bubbles that may be present in the stream due to their natural upward buoyant tendency. Any bubbles are therefore more likely to move quickly past the sensor in the chamber with minimal sensor interference.

A wide working range for the flow cell is important. For example, in the case of lactose in dairy industry effluent, lactose concentrations are characterized by rapid fluctuations spanning 0.1-12% w/v (corresponding to 2921 to 350,544 µM) due to short-lived periods of high loss interspersed with periods of clear discharge. Large fluctuations in lactose concentration mean a programmable auto-dilution system is required to maintain the biosensor's optimal performance and for regular re-calibration of the biosensor. Such automated systems are constrained by the need to minimize analysis time, buffer usage and effluent volumes (since these may have to be stored locally). Therefore, a system containing a biosensor with an increased working range, reduced interference from air bubbles and leaks, multiple SPCE biosensors and minimized electrical background noise represents a significant advantage for the practical monitoring of lactose loss in the dairy industry. The flow cell of the present disclosure is expected to provide similar benefits for a wide range of other electrochemical biosensor applications.

The flow cell of the present disclosure may be used for the determination of a wide variety of chemicals present in a flow stream. Potential applications of enzymatic biosensors in process control include diverse compounds of importance such as sugars, alcohols, and amino acids. In the agro-food industry, biosensor applications include food safety (the detection of pesticides, fertilizers and other pollutants), food anti-nutrient detection (oxylate, amygdalin, glucoalcalides), food quality (glucose, fructose, lactose, lactate, lactulose, glutamate, lysine, malate, ethanol, glycerol, catechol, cholesterol, citric acid, lecithin) and food freshness (polyphenols, short chain fatty acids, ornithine, amines, hypoxanthine, lactic acid, glucose, sucrose and isocitrate). It will be appreciated that the flow cell of the present disclosure may have an array of biosensors where each biosensor measures the concentration of a different chemical.

The use of the flow cell of the present disclosure is expected to reduce processing costs, minimize waste, reduce the environmental impact of many industrial processes, and reduce energy consumption. The flow cell is able to guide product recovery initiatives including the optimization of start-up and shut-down processes, clean-in-place processes, and the identification of system failures, leaks and spills.

The present disclosure is now further described with reference to the Figures. It will be appreciated that the present disclosure as claimed is not intended to be limited in any way by embodiments of the present disclosure shown in the Figures.

Figure 1:
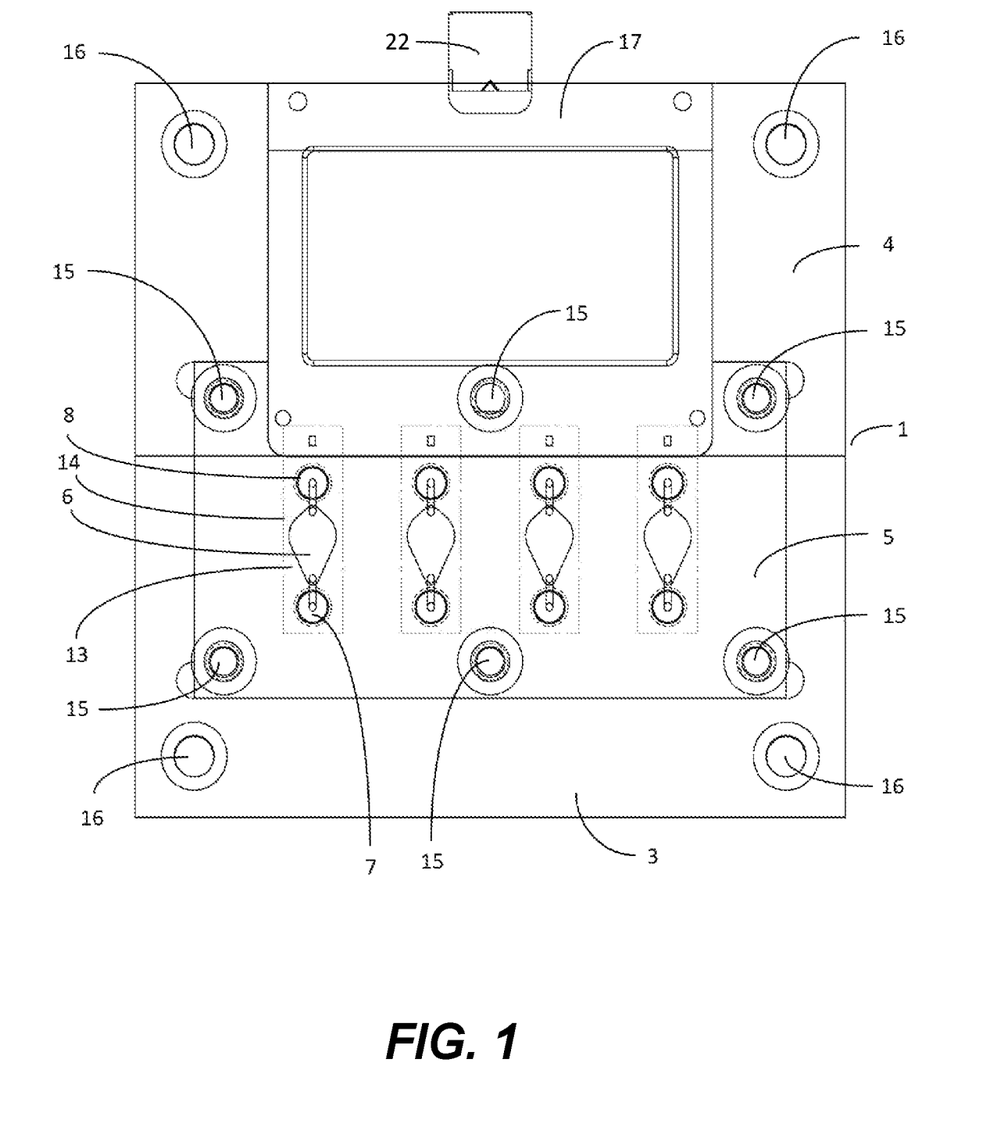
FIG. 1 is a front view of a flow cell according to one embodiment.
Figure 2:
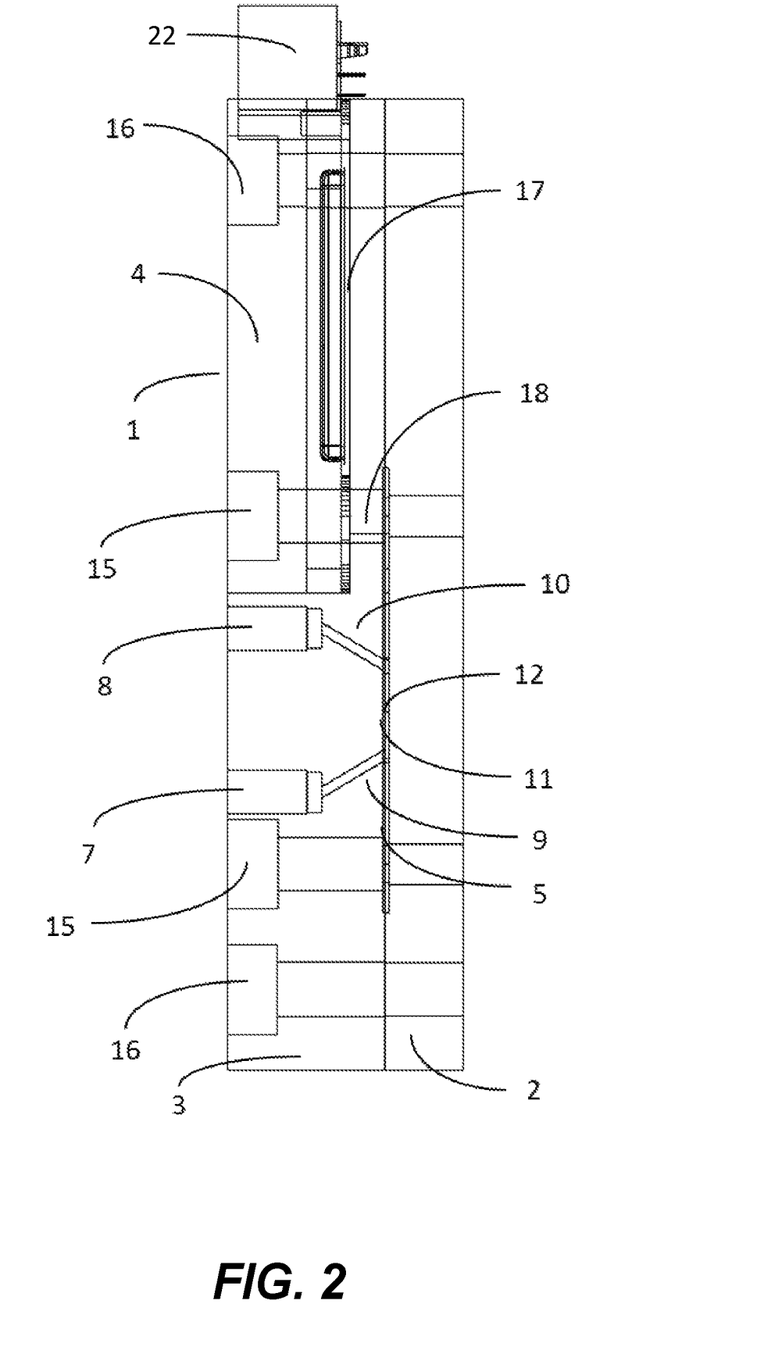
FIG. 2 is a side view of the flow cell shown in FIG. 1.

FIGS. 1 and 2 show a flow cell 1 of the present disclosure having a first section 2, a second section 3 and a cover 4. FIG. 1 is a front or plan view of the flow cell 1. The second section 3 and the cover 4 are visible from this view, but the first section 2 is located behind and so is not visible. The first section 2 can, however, clearly be seen in the side view of the flow cell 1 in FIG. 2. The first section 2, the second section 3 and the cover 4 are typically made from an acrylic material using a Computer Numerical Control (CNC) machine.

Figure 4B:
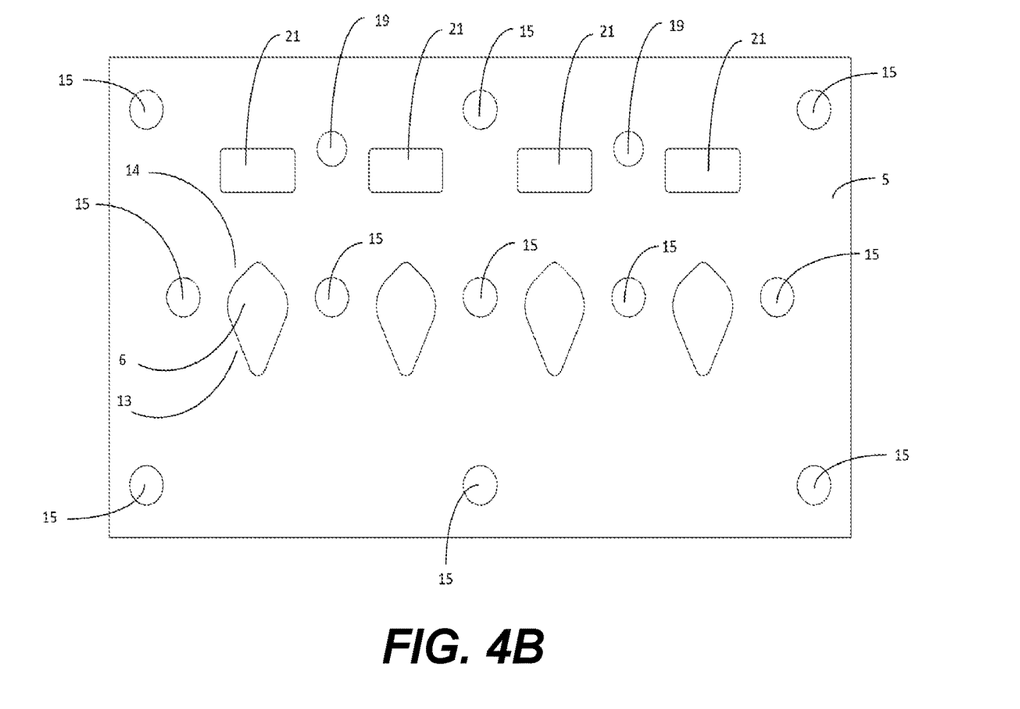
FIG. 4B is a perspective view showing an alternative embodiment gasket having an array of four openings for defining four fluid chambers.
Figure 4C:
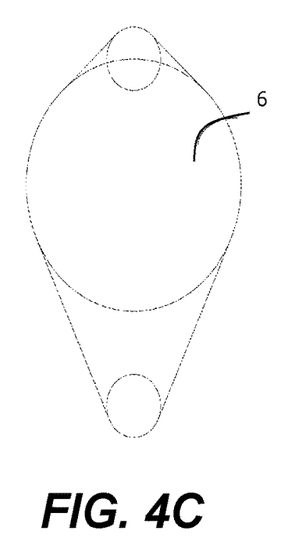
FIG. 4C is a schematic showing geometric features of the exemplary teardrop shape openings in the gaskets of FIGS. 4A and 4B.

The body of a gasket 5 is shown in FIG. 4B, and comprises an array of four teardrop-shaped apertures 6. The gasket 5 is preferably comprises a deformable resilient material. In the exemplary embodiment, the gasket 5 is a silicone gasket, made from 0.75-0.8 mm thick clear silicone sheet, which deforms to form a tight seal between the first section 2 and the second section 3 when these are pressed and secured together, for example, using fixing screws. The gasket 5 spaces a back face of the first body section 2 from a front face of the second body section 3. The back face of the first body section 2, front face of the second body section 3, and each aperture 6 in the gasket 5 defines a respective fluid chamber, with the perimeter of the chamber being substantially tear-shaped, as defined by the shape of the gasket aperture 6. The depth of the chamber substantially corresponds to the thickness of the gasket 5. In alternative embodiments, the chamber may be recessed into the first and/or second body sections, and/or the gasket may comprise a portion recessed into one or both body sections.

Each gasket aperture 6 and thereby each chamber is in fluid communication with a fluid inlet 7 and a fluid outlet 8 via a fluid inlet channel 9 and a fluid outlet channel 10. FIG. 4A shows a gasket 20 having a single opening 6, which can be used in an alternative single-sensor flow cell embodiment, or alternatively the flow cell may comprise a plurality of gaskets, each gasket defining a single fluid chamber. It will be appreciated that the array of sensors in the flow cell may comprise any number of sensors, for example, up to eight sensors. FIG. 4B shows a gasket 5 with four tear-shaped apertures for use in the flow cell 1 of FIGS. 1 and 2.

As can be seen in FIG. 2, fluid inlet channel 9 and fluid outlet channel 10 are both oriented at an angle of about 60° to the plane of the gasket 5, with the inlet passage 9 and outlet passage 10 being angled in opposite directions such that they mirror each other about a plane perpendicular to the gasket 5 (a horizontal plane in use). In alternative embodiments, the inlet and outlet passages 9, 10 may be inclined at an angle other than 60 degrees. In the embodiment shown, the angle of inclination of the inlet and outlet channels 9, 10 are the same (in opposite directions), but in alternative embodiments, the inlet passage 9 may be inclined at a different angle to the outlet passage 10.

An SPCE biosensor 11 is located in a chamber 12 (not easily discernable in FIG. 2) such that the sensor 11 is in fluid communication with the chamber, so that fluid in the chamber contacts the sensor 11. In the embodiment shown, the chambers 12 are provided in the second body section 3, but alternatively they may be provided in the first body 2. In the embodiment shown, the chamber and the sensors 11 are arranged along the vertical plane of the gasket 5, at the interface between the first and second body sections 2, 3; however, alternatively the chamber and/or the sensor may be otherwise oriented, for example, at right angles to the gasket plane.

In use, the flow cell 1 is preferably orientated vertically as shown in FIG. 2 such that fluid enters the chamber from a fluid inlet 7 and the fluid inlet channel 9 and then flows in an upward direction across the biosensor 11. The fluid then flows out of the chamber 12 though the fluid outlet channel 10 and a fluid outlet 8. This vertical orientation of the flow cell 1, having the fluid outlet 8 above the fluid inlet 7, is desirable because any bubbles that might be present in the fluid will naturally tend to rise and move in the same direction as the fluid flow therefore leading to reduced interference of biosensor measurements.

Each inlet passage 9, respective chamber, and respective outlet passage 10 together defines a fluid flow path. The fluid flow path along the inlet passage and the chamber forms an angle of about 120°, similarly, the fluid flow path along the chamber and outlet passage forms an angle of about 120°. However, in alternative embodiments the fluid flow path along the inlet passage and the chamber may form an alternative an angle of at least about 105°, and the fluid flow path along the chamber and outlet passage may form an angle of at least about 105°. The angle of fluid inlet channel 9 and fluid outlet channel 10 also contributes to reduced interference because the flow is more likely to be laminar flow, with reduced eddies and turbulence compared to fluid flow that would enter and/or leave the chamber at 90°.

In the embodiment shown, the inlet and outlet channels 10 are cylindrical channels with an internal diameter of about 1.2 mm. Referring to FIG. 4C, the gasket apertures 6 have a tear drop shape represented by three vertically aligned circles small top and bottom circles with a diameter of about 2 mm with a center spacing of about 11 mm, and a larger circle overlapping the top circle, having a diameter of 8 mm and a center spacing with the top circle of about 4 mm. Each aperture 6 is then defined by circle perimeters and tangential lines connecting the circles. The flow cell 1 and gasket 5 are designed to be used with flow rates of up to 1800 μl/min (about 30 μL s$^{-1}$), it will be understood that other dimensions or proportions are possible for the channels and chambers, depending on the application of the flow cell, for example, the flow rates required and the properties of the fluid, and the sensor dimensions.

The teardrop shape of the openings 6 has also been found to significantly reduce problems associated with turbulent fluid flow. When fluid enters the chamber 12, it is guided by the shape of the opening 6. The narrow end 13 of the opening 6 allows fluid entering the chamber 12 to gradually expand thereby encouraging laminar flow. The wide end 14 of the opening 6 allows for rapid exit of the fluid, which also encourages laminar flow through the chamber 12.

Screw holes 15 are shown where screws can be affixed for securing the first section 2, the second section 3 and the cover 4 together. These are also shown in the schematic representations of FIGS. 3A-3C. Corner holes 16 enable the flow cell 1 to be held securely in a cabinet when in use. Other fastening methods are envisaged for securing the first section 2 relative to the second section 3, for example, a snap fastener, a clip, or an adhesive.

Figure 3A:
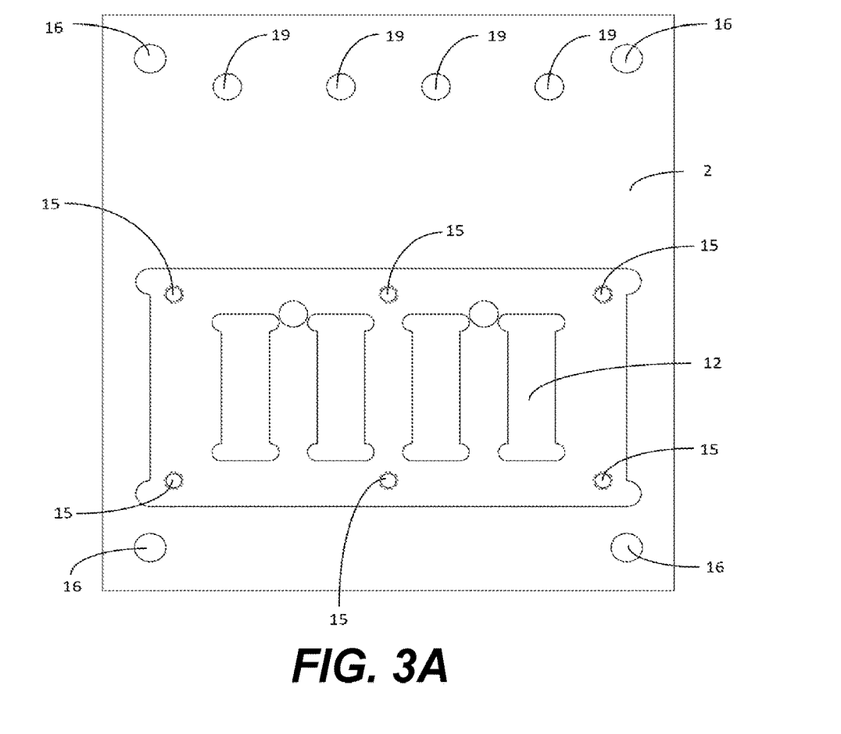
FIG. 3A is a schematic view of the first section of the flow cell of FIGS. 1 and 2.
Figure 3B:
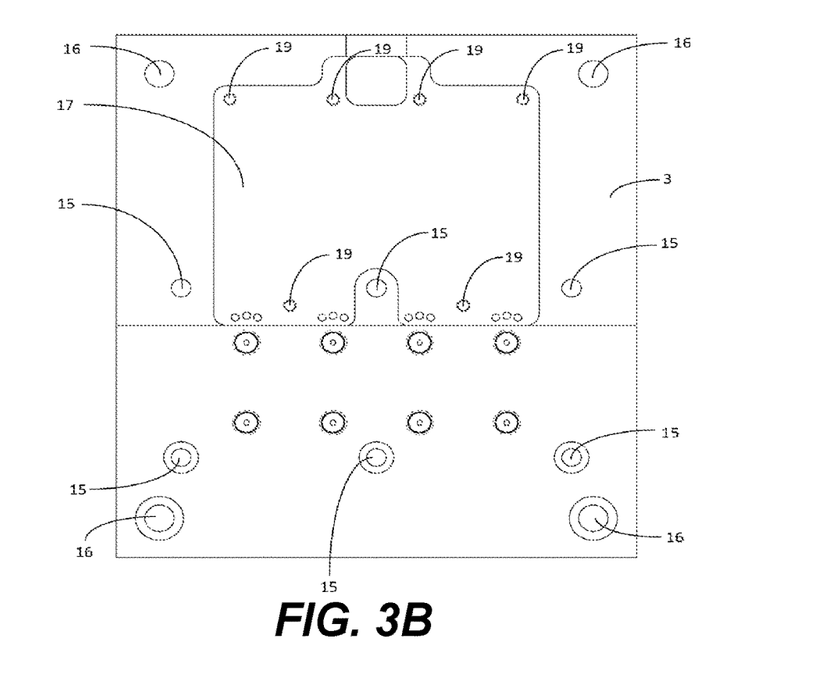
FIG. 3B is a schematic view of the second section of the flow cell of FIGS. 1 to 3A.
Figure 3C:
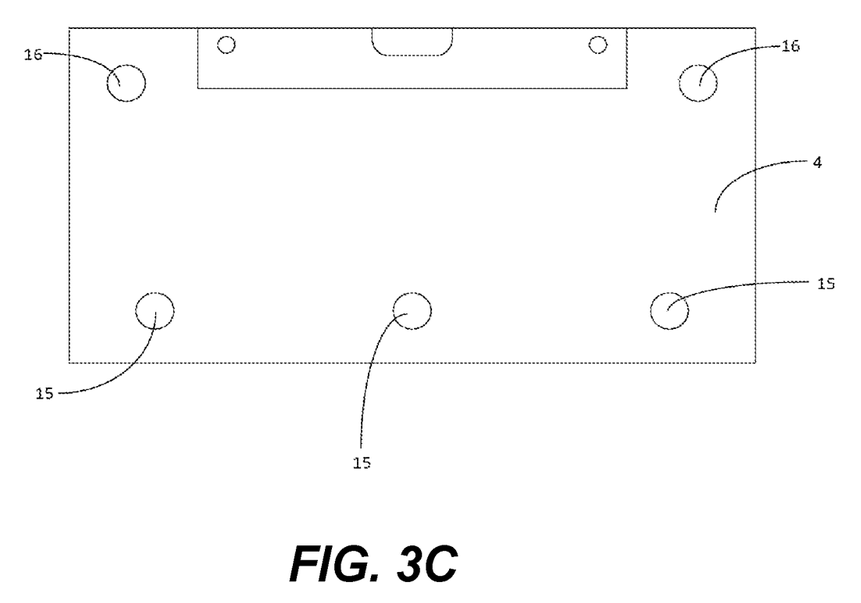
FIG. 3C is a schematic view of a cover of the flow cell of FIGS. 1 to 3B.

The flow cell 1 comprises a printed circuit board (PCB) 17 shown in FIG. 2 connected by a series of spring contact probes 18 in any suitable arrangement, to the SPCE biosensor 11 located in each chamber 12. In alternative embodiments other electrical contacts are envisaged, for example, an edge card connector. The biosensor 11 takes measurements, transmits an electrical signal to the PCB 17, which is preferably a potentiostat printed circuit board. The gasket 5 comprises a plurality of rectangular openings 21 in addition to the chamber apertures 6. These openings 21 allow for electrodes of the biosensors 11 to connect to the PCB 17. The PCB in turn transmits data via a data port 22 to a data processor (not shown). The data port may be any suitable port, for example, a PS/2 mini DIN connector; however other types of serial ports are envisaged such as USB ports. Alternatively, the data may be transmitted wirelessly to the data processor. FIGS. 3A and 3B show screw holes 19 for securing the PCB 17 to the flow cell 1.

FIGS. 6 to 8B show an alternative embodiment flow cell 101 with the data port 122 encased for improved protection rather than protruding from the top of the flow cell, and an alternative securing arrangement including five additional screw holes for securing the first section 2, the second section 3 and the cover 4 together. The gasket also contains five corresponding additional screw holes. Component parts in the embodiment of FIGS. 6 to 8B are indicated using like reference numbers compared to the embodiment of FIGS. 1 to 4B, but with the addition of 100.

Biosensors for determining lactose concentration in a fluid were prepared by immobilizing cellobiose dehydrogenase (CDH) from *Phanerochaete sordida* onto SPCEs. The performance of the SPCEs was tested using two electrochemical flow cells, a commercially available methacrylate wall jet flow cell (DropSens, ref. FLWCL) and the flow cell of the present disclosure.

Figure 5:
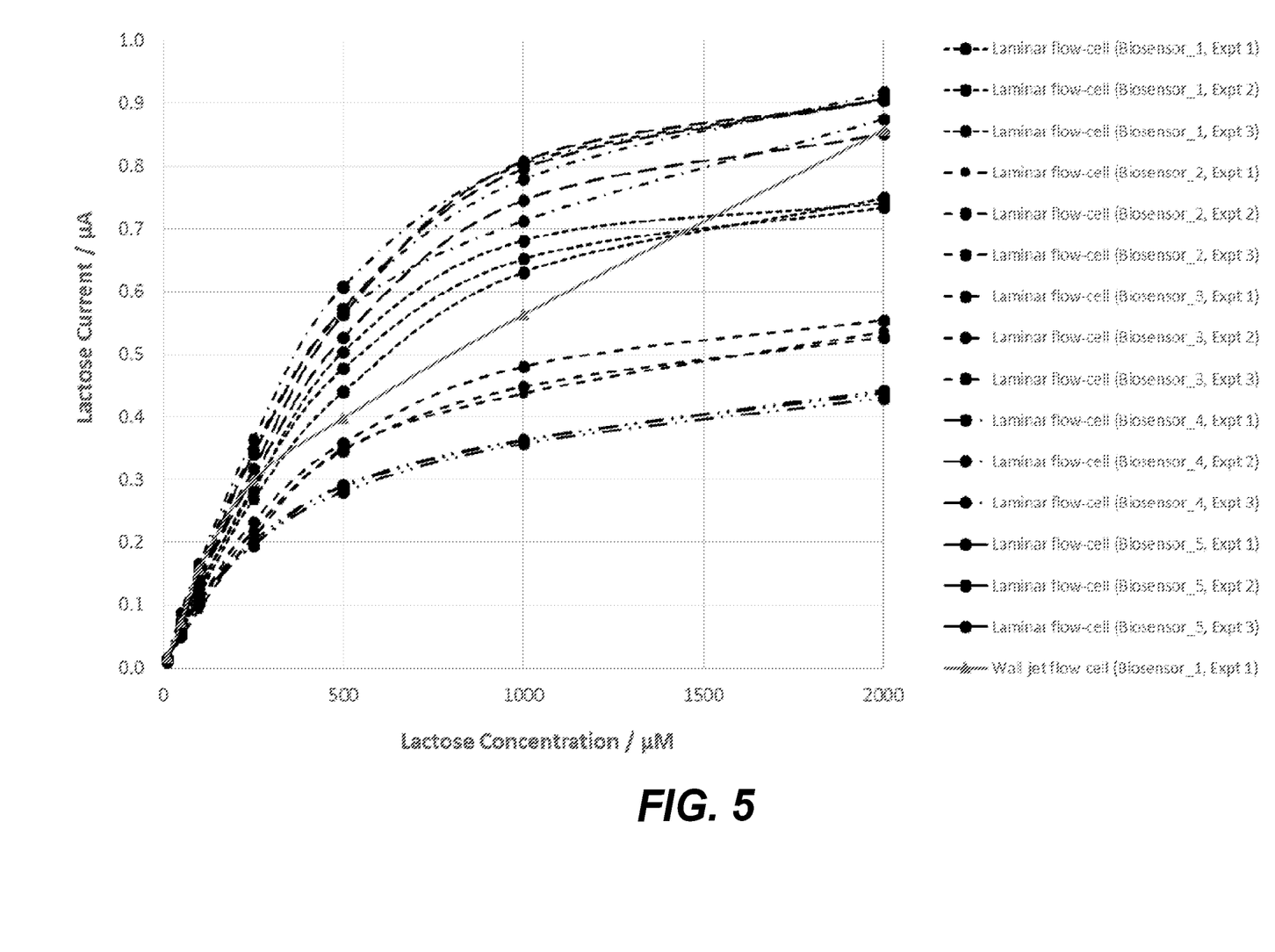
FIG. 5 is a graph of calibration curves for a lactose containing solution, created using experimental data obtained using the flow cell of FIGS. 1 to 4C.
Figure 6:
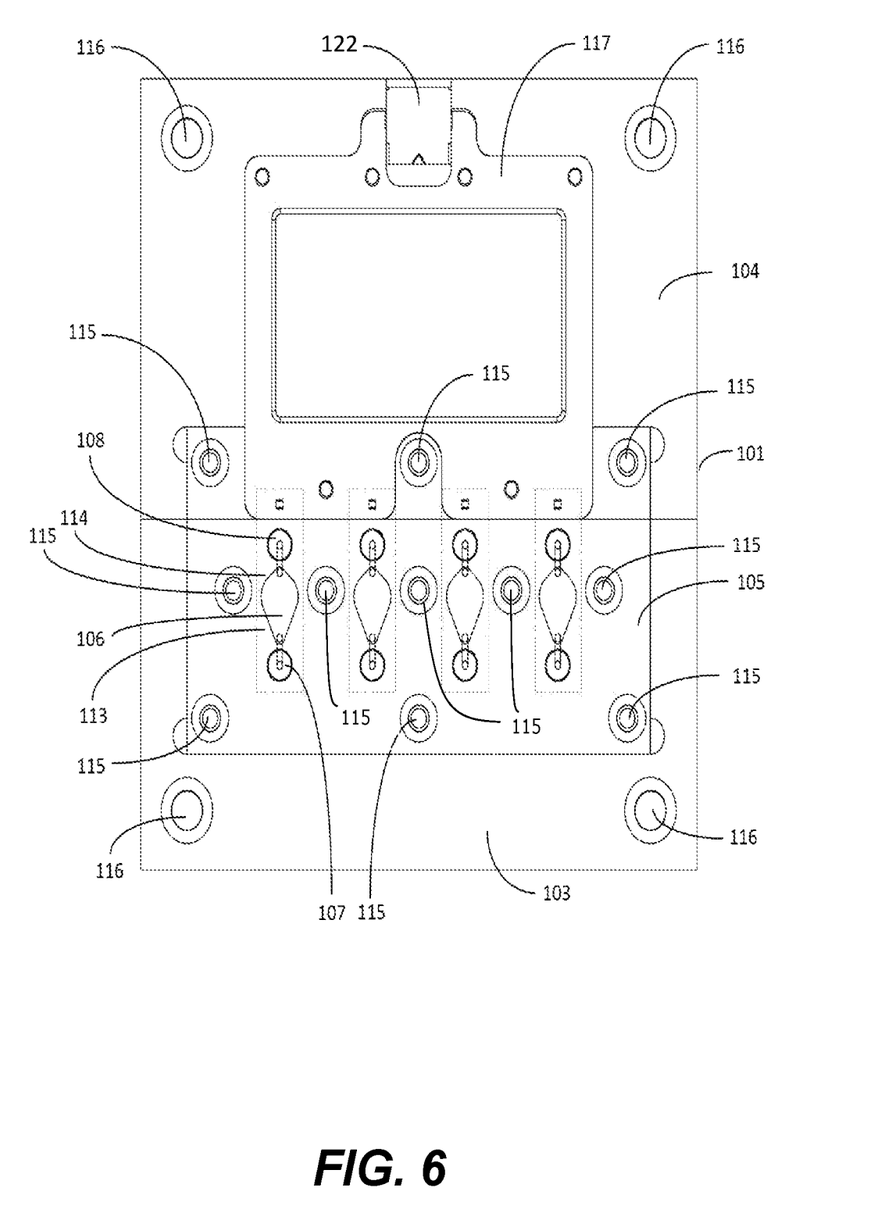
FIG. 6 is a front view of an alternative embodiment flow cell with encased data port and alternative securing arrangement.
Figure 7:
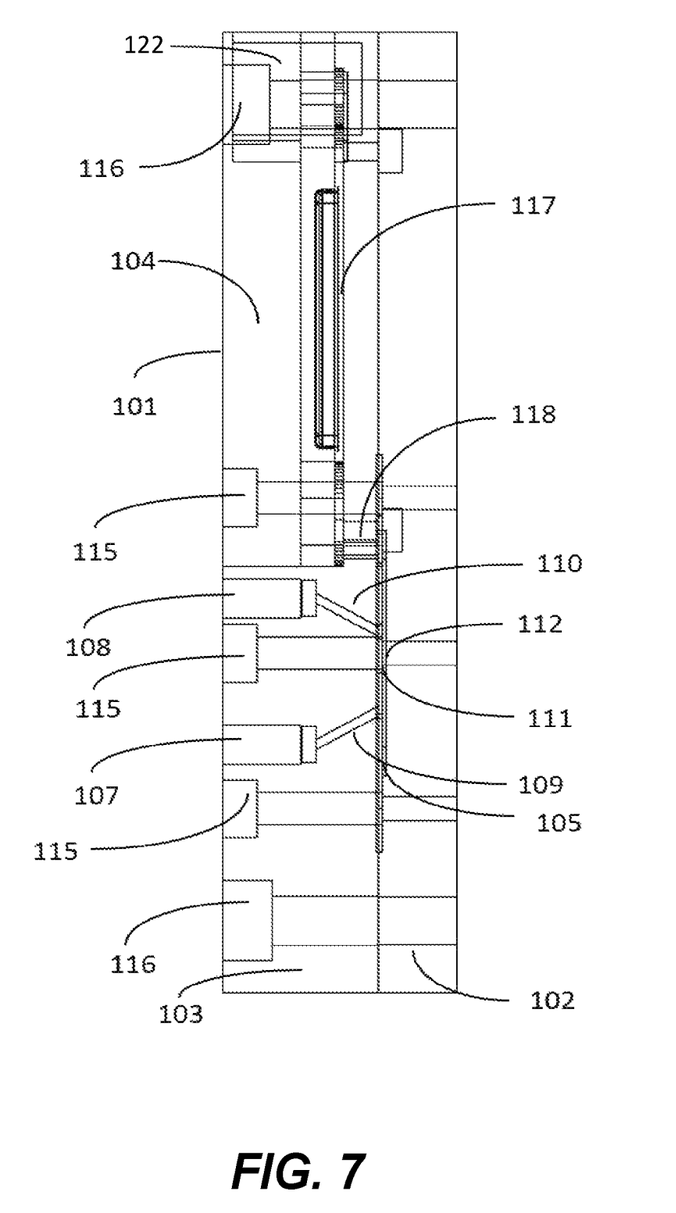
FIG. 7 is a side view of the flow cell shown in FIG. 6.
Figure 8A:
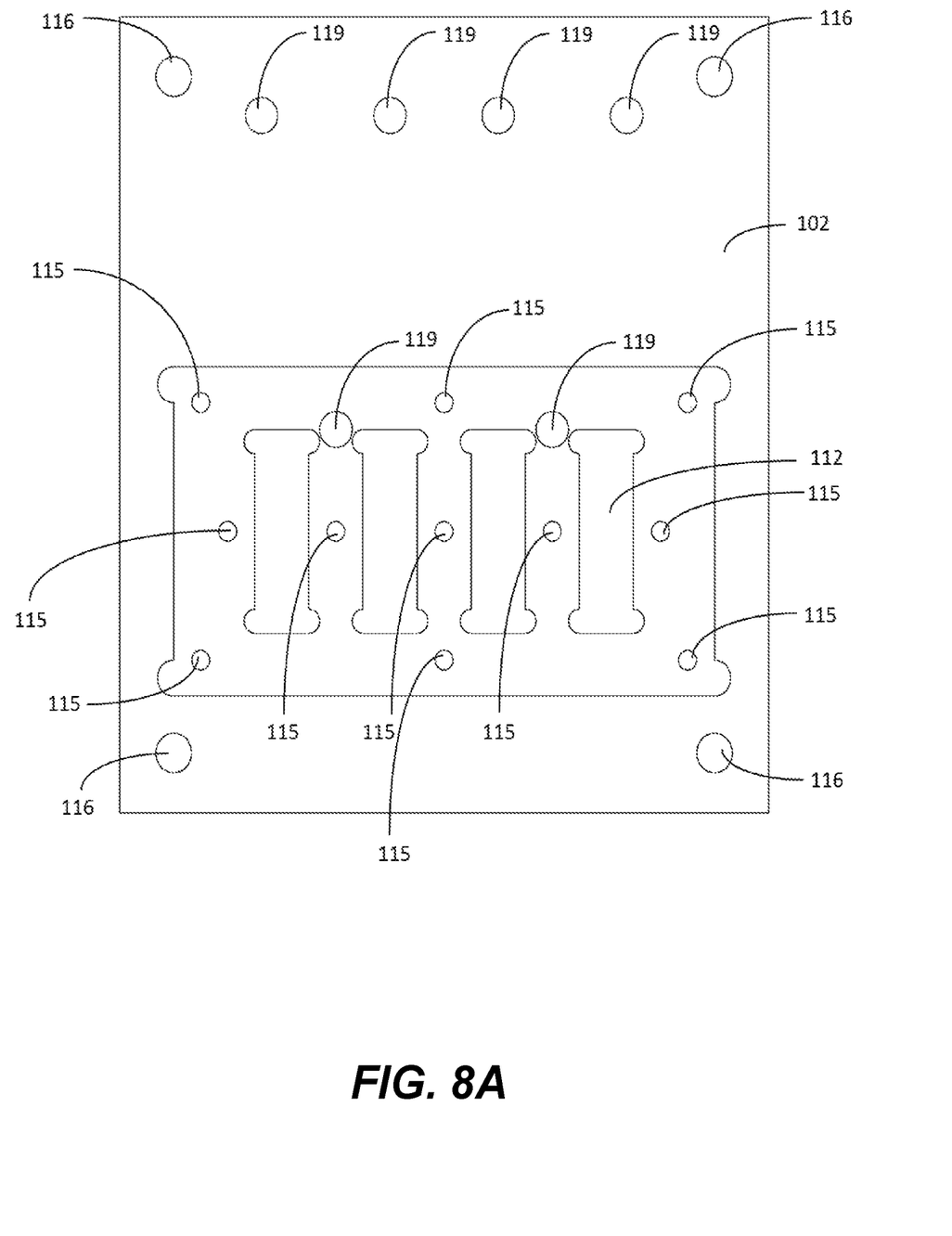
FIG. 8A is a schematic view of the first section of the flow cell of FIGS. 6 and 7.
Figure 8B:
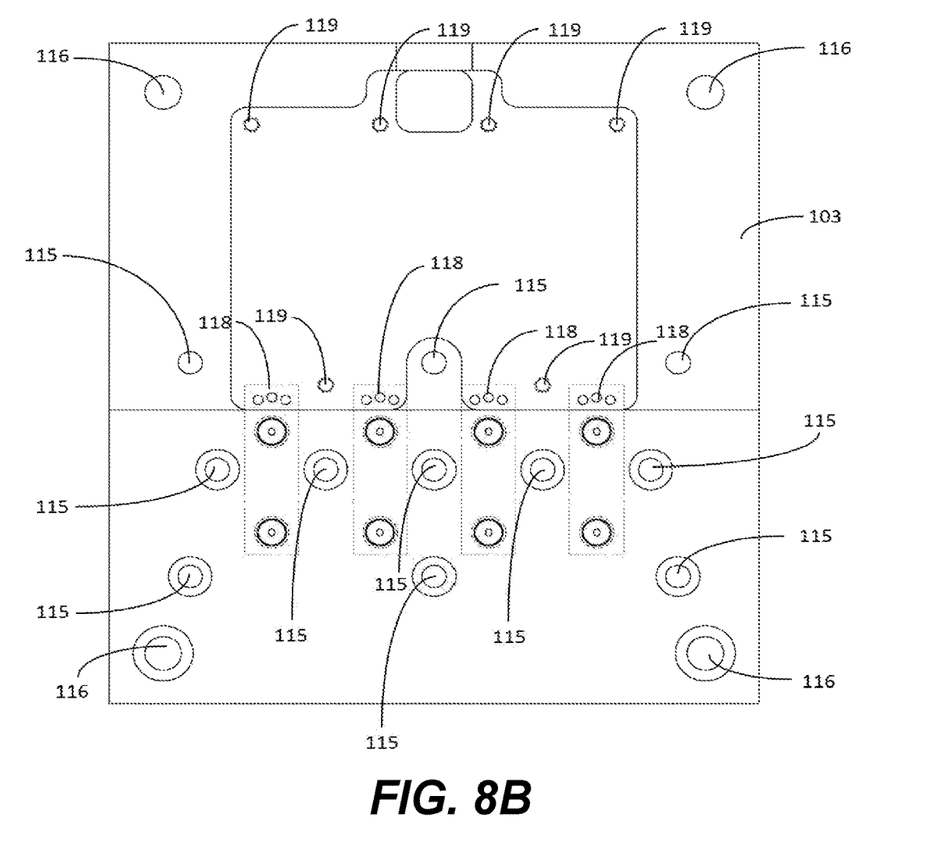
FIG. 8B is a schematic view of the second section of the flow cell of FIGS. 1 to 8A.
Figure 8C:
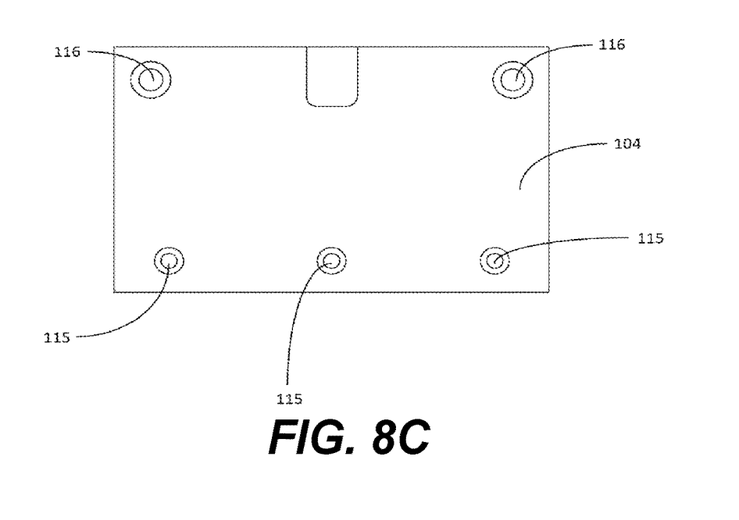
FIG. 8C is a schematic view of a cover of the flow cell of FIGS. 6 to 8B.

A series of lactose calibration standards (10 to 2000 μM) were measured using the flow cell of the present disclosure (5 biosensors with 3 repeat measurements of each concentration, n=15) and the wall jet flow cell (1 biosensor only with 1 measurement of each concentration, n=1) to produce a series of calibration curves (see FIG. 5). The data was partially analyzed using two models, a linear regression model and a non-linear regression model.

The linear regression analysis of the lactose calibration standards between 10 and 500 μM for the flow cell of the present disclosure produced an average correlation coefficient of $R^2=0.9605$ (n=15). The accuracy (root-mean-square error (RMSE)) of measuring a range of test lactose concentrations (29.20, 146, 204.4, 350.6 and 700 μM) using the flow cell is shown in Table 1.

TABLE 1

| | Flow cell accuracy data using a linear regression analysis | | | | | |
|---|---|---|---|---|---|---|
| Linear model [Lactose]/uM | RMSE Biosensor 1 | Biosensor 2 | Biosensor 3 | Biosensor 4 | Biosensor 5 | average |
| 29.20 | 2.99 | 10.41 | 8.80 | 31.86 | 7.31 | 12.27 |
| 146.00 | 45.23 | 56.69 | 47.25 | 94.30 | 34.60 | 55.61 |
| 204.40 | 57.45 | 62.12 | 50.72 | 95.15 | 40.83 | 61.25 |
| 350.60 | 40.35 | 37.40 | 25.61 | 49.53 | 13.37 | 33.25 |
| 700.00 | 87.37 | 135.52 | 123.58 | 151.89 | 120.33 | 123.74 |

The non-linear regression model used to analyses the data from the flow cell and was found to provide improved accuracy for lactose measurements, as shown in Table 2.

TABLE 2

| | Flow cell accuracy data using a non-linear regression analysis | | | | | |
|---|---|---|---|---|---|---|
| Non-linear model [Lactose]/uM | RMSE Biosensor 1 | Biosensor 2 | Biosensor 3 | Biosensor 4 | Biosensor 5 | average |
| 29.20 | 7.15 | 2.77 | 3.28 | 8.96 | 4.70 | 5.37 |
| 146.00 | 3.84 | 12.06 | 9.83 | 28.45 | 8.51 | 12.54 |
| 204.40 | 12.76 | 19.71 | 12.73 | 28.74 | 12.75 | 17.34 |
| 350.60 | 13.39 | 15.18 | 20.56 | 6.83 | 8.88 | 12.97 |
| 700.00 | 101.51 | 18.47 | 83.96 | 70.68 | 43.02 | 63.53 |

The wall jet flow cell was observed to be susceptible to trapping of air bubbles and leakage of buffer. This system had to be stopped to clear bubbles, and buffer leakage accelerated corrosion of the connector plug attached to the biosensor. These problems are significantly reduced in the laminar flow cell as it contains a vertically directed flow path and the biosensor connector fittings are located above the flow path, thus, isolating them from the carrier fluids, leading to trouble-free operation. For these reasons, the wall jet flow cell produces less accurate data than the laminar flow cell. A preliminary linear regression analysis of the lactose calibration standards (10 to 500 µM) measured using the wall-jet flow cell produced a correlation coefficient of $R^2=0.9251$ (n=1), which is lower than that produced by the laminar flow cell $R^2=0.9605$ (n=15). Hence, the wall jet flow cell is likely to be less accurate for lactose measurements.

Use of the flow cell of the present disclosure and the non-linear regression model has shown that lactose concentrations can be measured over a 29.2 to 700 µM working range with an acceptable level of uncertainty. The combination of the flow cell and non-linear model means the auto-dilution system of the lactose biosensor can be optimized so that it uses a pre-defined dilution factor (e.g., 500 fold dilution to ensure that all lactose measurements are within the working range of the biosensor) that minimizes buffer usage, effluent volumes and analysis time (as less sample handling time is required). The auto-dilution system also requires fewer components (e.g., valves, pumps and containers). This combination results in more frequent data points for the end user and directly leads to more efficient lactose monitoring over an industrially applicable range (e.g., 0.1 to 12% lactose) for dairy-processing plants. A flow rate of 20 µL s$^{-1}$ (1200 µL min$^{-1}$) created a laminar flow across the sensor during sample measurement.

As can readily be appreciated, the flow cell assembly of the present disclosure has a number of advantages over devices for monitoring dairy processing streams. These include:

The working range of the biosensor is increased. The working range of the biosensor describes the range of concentrations over which it can accurately measure a concentration perturbation with acceptable uncertainty.

Significantly less interference due to air bubbles. The custom design has a vertical upwards flow path so that the buoyant tendency of a gas bubble and flow are working in the same direction.

Significantly reduced leakage. The design of the flow cell reduces corrosion of the connector plugs attached to a SPCE biosensor leading to increased sensor lifetime (i.e., each sensor can be re-used more times).

Reduced maintenance requirements for end-users of the technology through the incorporation of multiple SPCE biosensors in one flow cell, which can be used on a rotational basis to extend the period between replacements.

Reduced electrical noise due to the inclusion of a reusable shielded potentiostat printed circuit board (PCB) into the flow cell removing the need for electrical wiring to an external potentiostat.

Currently there is no reliable method for on-line monitoring of lactose in dairy processing. Lactose has traditionally been overlooked in the dairy industry because milk quality and price are determined by fat and protein content. The applicant has created a novel lactose-based process control point for the dairy industry that can be used for the continuous on-line lactose monitoring for dairy processing and wastewater streams, giving:

Increased process control
Maximized profits
Minimized waste
Enhanced environmental outcomes
Reduced energy consumption As used in this specification, the words "comprises," "comprising," and similar words, are not to be interpreted in an exclusive or exhaustive sense. In other words, they are intended to mean "including, but not limited to."

Although the present disclosure has been described by way of example, it should be appreciated that variations and modifications may be made without departing from the scope of the present disclosure as defined in the claims. Furthermore, where known equivalents exist to specific features, such equivalents are incorporated as if specifically referred in this specification.

The invention claimed is:

1. A flow cell for continuous flow, on-line measurements, the flow cell comprising:
a first body section and a second body section, and a gasket arranged to seal between the first body section and the second body section;
wherein the gasket, the first body section, and the second body section together define one or more chambers, each chamber having a perimeter with a narrower end and a rounded wider end;
each chamber having an inlet passage in fluid communication with the chamber, an outlet passage in fluid communication with the chamber, and a biosensor arranged in fluid communication with the chamber;
wherein each inlet passage directs fluid into the respective chamber proximal the narrower end of the chamber at an angle of between about 45° to about 75° relative to a plane of the gasket and each outlet passage directs fluid flow out of the wider end of the chamber at an angle between about 45° to about 75° relative to the plane of the gasket, the inlet passage and outlet passage being angled in opposite directions; and
the flow cell further comprising an electronic measurement system in electrical communication with each of the one or more biosensors and configured to transmit data to a data processor.

2. The flow cell of claim 1, wherein the electronic measurement system comprises a potentiostat printed circuit board.

3. The flow cell of claim 1, wherein the gasket comprises one or more apertures, the apertures shaped to define the perimeter of a respective chamber.

4. The flow cell of claim 3, wherein a depth of each chamber substantially corresponds to a thickness of the gasket.

5. The flow cell of claim 1, wherein the inlet and outlet passages are provided in the first body section.

6. The flow cell of claim 1, wherein the second body section comprises one or more recesses to receive the biosensor(s).

7. The flow cell of claim 1, wherein each chamber is teardrop-shaped.

8. The flow cell of claim 1, wherein the gasket comprises a deformable material.

9. The flow cell of claim 8, wherein the gasket comprises a resilient material.

10. The flow cell of claim 1, wherein each inlet passage, respective chamber, and respective outlet passage defines a fluid flow path, the fluid flow path along the inlet passage and the chamber forming an angle of at least about 105°, and the fluid flow path along the chamber and outlet passage forming an angle of at least about 105°.

11. The flow cell of claim 1, wherein each inlet passage is configured to be below the associated outlet passage.

12. The flow cell of claim 11, wherein each inlet passage, respective chamber, and respective outlet passage defines a fluid flow path in a generally upwards direction.

13. The flow cell of claim 1, wherein the inlet and outlet passages and chambers enable continuous, substantially laminar flow of liquid along each chamber.

14. The flow cell of claim 1, wherein each inlet passage directs fluid into the respective chamber and/or each outlet passage directs fluid flow out of the respective chamber at an angle relative to a plane of the gasket of between about 55° and about 65°.

15. The flow cell of claim 14, wherein each inlet passage directs fluid into the respective chamber and/or each outlet passage directs fluid flow out of the respective chamber at an angle relative to the plane of the gasket of about 60°.

16. The flow cell of claim 1, wherein the flow cell comprises two to eight biosensors.

17. The flow cell of claim 16, wherein the flow cell comprises an array of four biosensors.

18. The flow cell of claim 1, wherein each biosensor comprises a sensor molecule immobilized on a screen-printed electrode.

19. The flow cell of claim 18, wherein the sensor molecule is selected from a group comprising microorganisms, organelles, cell receptors, enzymes, antibodies, and nucleic acids.

20. The flow cell of claim 1, wherein the flow cell comprises a plurality of biosensors and each biosensor is capable of determining a concentration of a chemical in a fluid independently of each other biosensor.

21. The flow cell of claim 20, wherein at least one of the biosensors is capable of determining the concentration of any one or more of a group comprising pesticides, fertilizers, oxylate, amygdalin, glucoalcalides, glucose, fructose, lactose, sucrose, lactate, lactulose, glutamate, lysine, malate, ethanol, glycerol, catechol, cholesterol, citric acid, lecithin, polyphenols, short chain fatty acids, ornithine, amines, hypoxanthine, lactic acid, and isocitrate.

22. The flow cell of claim 21, wherein at least one of the biosensors is capable of determining the concentration of lactose.

23. The flow cell of claim 1, further comprising a cover for protection of the electronic measurement system.

24. A method for determining a concentration of a chemical in a fluid obtained from a process stream comprising:
placing a flow cell in fluid communication within a flow of fluid from a process stream, such that there is a generally continuous flow of fluid through the flow cell, wherein the flow cell comprises:
a first body section and a second body section, and a gasket arranged to seal between the first body section and the second body section;
wherein the gasket, the first body section, and the second body section together define one or more chambers, each chamber having a perimeter with a narrower end and a rounded wider end;
each chamber having an inlet passage in fluid communication with the chamber, an outlet passage in fluid communication with the chamber, and a biosensor arranged in fluid communication with the chamber;
wherein each inlet passage directs fluid into the respective chamber proximal the narrower end of the chamber at an angle of between about 45° to about 75° relative to a plane of the gasket and each outlet passage directs fluid flow out of the wider end of the chamber at an angle between about 45° to about 75° relative to the plane of the gasket, the inlet passage and outlet passage being angled in opposite directions; and
the flow cell further comprising an electronic measurement system in electrical communication with each of the one or more biosensors and configured to transmit data to a data processor; and
transmitting measurement data from the electronic measurement system to a processor.

25. The method of claim 24, wherein the chemical is selected from a group comprising pesticides, fertilizers, oxylate, amygdalin, glucoalcalides, glucose, fructose, lactose, sucrose, lactate, lactulose, glutamate, lysine, malate, ethanol, glycerol, catechol, cholesterol, citric acid, lecithin, polyphenols, short chain fatty acids, ornithine, amines, hypoxanthine, lactic acid, and isocitrate.

26. The method of claim 24, wherein the fluid is obtained from a dairy processing stream.

27. The method of claim 24, wherein the, or each, biosensor is used to determine the concentration of the chemical, which biosensor has electrodes that are in electrical communication with a potentiostat printed circuit board.

28. The method of claim 27, wherein the data processor processes the data received from the biosensor and produces an output to enable a controller to adjust one or more parameters of a process that produces the process stream.

29. A system comprising:
a flow cell comprising:
a first body section and a second body section, and a gasket arranged to seal between the first body section and the second body section;
wherein the gasket, the first body section, and the second body section together define one or more chambers, each chamber having a perimeter with a narrower end and a rounded wider end;
each chamber having an inlet passage in fluid communication with the chamber, an outlet passage in fluid communication with the chamber, and a biosensor arranged in fluid communication with the chamber;
wherein each inlet passage directs fluid into the respective chamber proximal the narrower end of the chamber at an angle of between about 45° to about 75° relative to a plane of the gasket and each outlet passage directs fluid flow out of the wider end of the chamber at an angle between about 45° to about 75° relative to the plane of the gasket, the inlet passage and outlet passage being angled in opposite directions; and
the flow cell further comprising an electronic measurement system in electrical communication with each of the one or more biosensors and configured to transmit data to a data processor,
wherein the flow cell is arranged in communication with fluid from a process stream, such to enable a generally continuous flow of fluid through the flow cell, a processor in communication with the flow cell electronic measurement system, and a controller configured to receive an output from the processer and adjust one or more parameters of a process that produces the process stream in response to the processor output, wherein the processor output is representative of a concentration of a chemical in the fluid obtained from the process stream.

* * * * *